United States Patent
Tirtowidjojo et al.

(10) Patent No.: US 10,189,756 B2
(45) Date of Patent: Jan. 29, 2019

(54) ADIABATIC PLUG FLOW REACTORS AND PROCESSES INCORPORATING THE SAME

(71) Applicant: BLUE CUBE IP LLC, Midland, MI (US)

(72) Inventors: Max M. Tirtowidjojo, Midland, MI (US); Hua Bai, Midland, MI (US); Debashis Chakraborty, Midland, MI (US); Juergen Eiffler, Midland, MI (US); Heinz Groenewald, Midland, MI (US); Kurt F. Hirsekorn, Midland, MI (US); Manfred Kokott, Midland, MI (US); William J. Kruper, Midland, MI (US); Thomas U. Luebbe, Midland, MI (US); Thomas J. Parsons, Midland, MI (US); Avani Maulik Patel, Midland, MI (US); Marcus Wobser, Midland, MI (US)

(73) Assignee: BLUE CUBE IP LLC, Clayton, MO (US)

( * ) Notice: Subject to any disclaimer, the term of this patent is extended or adjusted under 35 U.S.C. 154(b) by 214 days.

(21) Appl. No.: 15/204,462

(22) Filed: Jul. 7, 2016

(65) Prior Publication Data
US 2016/0347692 A1 Dec. 1, 2016

Related U.S. Application Data (62) Division of application No. 12/901,383, filed on Oct. 8, 2010, now abandoned.

(60) Provisional application No. 61/250,023, filed on Oct. 9, 2009.

(51) Int. Cl.
| | | |
|---|---|---|
| C07C 17/20 | (2006.01) | |
| C07C 17/269 | (2006.01) | |
| C07C 21/18 | (2006.01) | |
| C07C 21/04 | (2006.01) | |
| B01J 19/00 | (2006.01) | |
| B01J 19/24 | (2006.01) | |

(52) U.S. Cl.
CPC .......... *C07C 17/206* (2013.01); *B01J 19/006* (2013.01); *B01J 19/0013* (2013.01); *B01J 19/0026* (2013.01); *B01J 19/2405* (2013.01); *B01J 19/2415* (2013.01); *C07C 17/269* (2013.01); *B01J 2219/00054* (2013.01); *B01J 2219/00063* (2013.01); *B01J 2219/00155* (2013.01); *B01J 2219/00162* (2013.01); *B01J 2219/00166* (2013.01); *B01J 2219/00247* (2013.01)

(58) Field of Classification Search
CPC ....... C07C 17/25; C07C 21/18; C07C 17/206; C07C 17/278; C07C 17/383
See application file for complete search history.

(56) References Cited

U.S. PATENT DOCUMENTS

| | | |
|---|---|---|
| 4,513,154 A | 4/1985 | Kurtz |
| 5,057,634 A | 10/1991 | Webster et al. |
| 6,031,141 A * | 2/2000 | Mallikarjuna ......... B01J 27/132 570/136 |
| 2009/0253946 A1 | 10/2009 | Van Der Puy |

FOREIGN PATENT DOCUMENTS

| | | |
|---|---|---|
| EP | 1018366 | 7/2000 |
| EP | 0905090 | 10/2011 |
| JP | 1997-020699 | 8/1998 |
| JP | 2001-246239 | 9/2001 |
| WO | 0058259 | 10/2000 |
| WO | WO2007117391 | 10/2007 |
| WO | WO2010045104 | 4/2010 |
| WO | 01064333 | 6/2010 |

OTHER PUBLICATIONS

JP2015-234573 Office Action dated Oct. 30, 2017.
PCT/US2010/052090 International Search Report dated May 16, 2011.

* cited by examiner

Primary Examiner — Jafar F Parsa
(74) Attorney, Agent, or Firm — Polsinelli PC (57) ABSTRACT

The present invention provides adiabatic plug flow reactors suitable for the production of chlorinated and/or fluorinated propene and higher alkenes from the reaction of chlorinated and/or fluorinated alkanes and chlorinated and/or fluorinated alkenes. The reactors comprise one or more designs that minimize the production of by-products at a desired conversion.

14 Claims, 4 Drawing Sheets

ADIABATIC PLUG FLOW REACTORS AND PROCESSES INCORPORATING THE SAME

FIELD

The present invention relates to plug flow reactors capable of adiabatic operation and suitable for conducting continuous, gas phase, free radical reactions to produce chlorinated and/or fluorinated propene and higher alkenes. Processes incorporating the same are also provided.

BACKGROUND

Tubular reactors are ubiquitous in the manufacture of commodity chemicals, in particular in processes wherein continuous operation is desired or required. The ideal flow condition in a tubular reactor is 'plug flow', and under such ideal conditions, the residence time in the reactor is the same for all elements of fluid and there is typically a uniform velocity profile across the radius of the reactor. Product mixing is also ideally limited to material the same age, i.e. mixing occurs in the radial direction only. That is, as the plug flows through the reactor, the plug components are perfectly mixed in the radial direction, with mixing in the axial direction being nonexistent.

While in practice, ideal plug flow does not occur, maintaining reasonably good plug flow (such that the flow profile closely resembles plug flow velocity profile) through tubular reactors provides significant benefits. For one, plug flow provides greater separation between reacted and unreacted material than non plug flow. This is desirable for processes where reaction rate is affected by reactant concentration. And, good plug flow permits precise control of residence time, which can be critical in processes where conversion and/or selectivity are sensitive to the same.

Many factors can impact the ability to provide plug flow conditions approximating ideal. For example, substantial mixing in the axial direction can reduce the quality of plug flow, as can wall friction and diffusion, etc. The effects of many of these can be mitigated by increasing the fluid velocity and/or reactor channel length. Achieving the right combination of residence time, efficient mixing and good plug flow can result in tubular reactors that are hundreds of meters long. Reactors of such length can then present additional difficulties in temperature control and heat transfer characteristics.

It would thus be desirable to provide a tubular reactor capable of approximating plug flow, while yet also providing optimal, e.g., residence time, heat transfer characteristics, temperature control and mixing.

BRIEF DESCRIPTION

Such a reactor is provided herein. More specifically, the reactor described herein can provide one or more of more accurate temperature control, minimization of heat transfer into and/or out of the reactor, appropriate residence times of reaction components and or optimized mixing. As a result, desired conversions and/or selectivities can be seen. The reactor is thus particularly well suited for reactions comprising thermally sensitive components such as catalysts that may otherwise exhibit reduced lifetimes, or reaction components that undesirably react or decompose at temperatures within the processing specifications of the process desirably carried out within the reactor.

In one aspect of the present invention, an adiabatic plug flow reactor suitable for use in a continuous, gas phase, free radical process for the production of chlorinated and/or fluorinated propene and higher alkenes is provided, wherein the reactor comprises a design that facilitates reduced backmixing and/or recirculation prior to entry into, or upon exit from, the reactor, or reduced formation of by-products during any backmixing that may occur. In some embodiments, the reactor may further comprise a design that minimizes the production of by-products at a desired conversion.

Several such designs are provided, including i) a design that minimizes heat transfer to and/or from the reactor; ii) a design that optimizes the flow of the reaction components at the boundary between the reaction components and at least a portion of at least one reactor tube wall; iii) a design that facilitates a reduction of the temperature of a reactor effluent to a temperature below which substantial formation of by-products does not occur, and/or iv) a design that allows the production rate of a process conducted in the reactor to be adjusted by controlling the temperature of the reactor effluent. Combinations of one or more of these may be utilized, in which case the benefits provided by one may be further leveraged, perhaps even synergistically, by addition of the other(s).

Since the present reactors are expected to provide time and cost savings to the continuous processes in which they are utilized, not only are processes utilizing the reactor provided, but the products produced thereby may be used to carry these advantages forward, i.e., to downstream processes, or to end-uses. And so, also provided herein are processes for the use of a chlorinated and/or fluorinated propene or higher alkene, which in some embodiments may be a chlorinated propene, produced in the present reactors to prepare a downstream product, which in some embodiments, may be 2,3,3,3-tetrafluoroprop-1-ene (HFO-1234yf) or 1,3,3,3-tetrafluoroprop-1-ene (HFO-1234ze).

BRIEF DESCRIPTION OF THE DRAWINGS

These and other features, aspects, and advantages of the present invention will become better understood when the following detailed description is read with reference to the accompanying drawings, wherein.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to bely any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not intended to limit the part being described limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant. It is to be understood that use of the term "plug flow" herein indicates that the reactor approximates ideal plug flow, not necessarily that ideal plug flow is achieved.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

The present invention provides an adiabatic plug flow reactor suitable for use in a continuous, gas phase, free radical process for the production of chlorinated and/or fluorinated propene and higher alkenes. Advantageously, the reactor comprises a design that minimizes the production of by-products, including decomposition products of reaction components that may foul the reactor. In so doing, the percent conversion of the reaction carried out within the reactor may be kept within a desired range. For example, in some embodiments, the conversion can be caused to increase less than about 5%, or less than about 2%, or even less than about 1%, so that a desired selectivity can be seen. Stated another way, at a limiting reagent conversion of at least about 5%, or at least about 10%, or at least about 15%, or even at least about 20%, selectivity to the desired product can be as high as about 70%, or about 75%, or about 80%, or even about 85% or greater. As such, the present tubular plug flow reactor is particularly well suited for conducting reactions for which an increase in percent conversion may typically indicate increased production of reaction by-products, and thus, reduced percent selectivity.

The reactors described herein may be utilized in any continuous gas-phase, free radical process, and in particular, are well suited for such reactions that are also homogeneous and exothermic. The reactors described herein are also particularly appropriately employed for reactions involving at least one limiting reactant having a desired conversion far from exhaustion of the same, e.g., conversions of less than 80%, or less than 40%, or even less than 20% of the limiting reactant. As discussed above, the present reactors are also particularly well suited for such reactions particularly susceptible to the formation of by-products, and the effects thereof on reaction selectivity, or comprising thermally sensitive components, e.g., that may react, or degrade, to form undesirable by-products. Thermally sensitive components may include, for example, reactants, products, catalysts, and even by-products which may further react or thermally degrade to form other by-products. Reactions comprising combinations of thermally sensitive components may also find benefit from being carried out in the present reactors. Even at such low conversions of limiting reagent, and when used to conduct reactions susceptible to the formation of by-products, the present reactors can provide selectivity to the desired product of at least about 70%, or about 75%, or about 80%, or even about 85% or greater.

One example of such reactions includes, but is not limited to, reactions that produce chlorinated and/or fluorinated propene and higher alkenes. Preferred alkenes include those having from about three to about six carbon atoms. Exemplary reactions include reactions of methanes, including chloromethanes, fluoromethanes or chlorofluoromethanes, having the formula $CH_{4-a-b}Cl_aF_b$, wherein each a and b are independently 0-3 and 4-a-b is greater than 0; and chloroethylenes or chlorofluoroethylenes to provide chlorinated and/or fluorinated propenes according to the formula $CH_{2-c-g}Cl_cF_g$=$CH_{1-d-h}Cl_dF_h$—$CH_{3-e-f}Cl_eF_f$ wherein c is 0-2, d is 0-1, e is 0-3, f is 0-3, and g is 0-2 while c+g≤2, d+h≤1, and e+f≤3. Particular exemplary reactions include the reaction of methyl chloride with perchloroethylene to provide 1,1,2,3-tetrachloropropene, the reaction of methyl fluoride with perchloroethylene to provide 1,1,2-chloro-3-fluoro-propene, and the reaction of methyl fluoride with triflurochloroethylene to provide 1,1,2,3-tetrafluoropropene. However, these are intended only to be exemplary and are not to be construed as limiting to the concepts described herein.

Many parameters are known in the chemical engineering art to be useful in adjusting the reaction conditions within tubular reactors, however, prior to the invention described herein, had either not been applied in a manner that resulted in a reduction in formation of by-products so that a desired conversion can be seen, and/or to reactions particularly in need thereof. That is, it has now been discovered how to design an adiabatic tubular reactor to be amenable for use in conducting continuous gas phase, free radical reactions comprising thermally sensitive reaction components, such as catalysts or initiators comprising chlorine, so that the reactions conducted therein have the desired percent conversions. Because of the unique chemistry involved in conducting continuous gas phase, free radical reactions comprising thermally sensitive reaction components, those of ordinary skill in the chemical engineering art would not necessarily consider adiabatic tubular reactors as good candidates within which to conduct them.

For example, processes for the production of chlorinated or fluorinated propenes may typically result in the formation of larger quantities of reaction by-products than conventional halogenation processes. That is, in conventional free radical halogenation reactions, reactor promoted backmixing or recirculation, such as that provided by jet stirred reactors, is typically considered to increase productivity of the reactor, without concurrent increases in byproduct formation [Liu et al, *Chemical Engineering Science* 59 (2004) 5167-5176]. In the present processes, such backmixing or recirculation would result in the formation of unacceptable amounts of by-products.

The formation of large quantities of by-products, in turn, can not only detrimentally impact process capacity and conversion, but can be problematic for other reasons as well, not the least of which being that the same can cause reactor fouling. Reactor fouling can effectively reduce the reactor volume available for the desired reaction to take place.

Undesirable time or cost expense may also be added to the process, via the cleaning necessitated for a reactor fouled to such an extent that a commercially acceptable throughput is no longer possible. Because formation of by-products is typically not an issue in conventional gas-phase free radical halogenations reactions, one of ordinary skill in the art would not expect solutions for the reduction of such byproducts by reducing or eliminating backmixing or recirculation to be applicable to the chlorination and/or fluorination reactions described herein.

The present improved reactors for the production of chlorinated and/or fluorinated propenes or higher alkenes that minimize the formation of by-products at least by minimizing or eliminating the amount of backmixing and/or recirculation that occurs in the reactor. In conventional gas-phase, free radical halogenation processes, backmixing and/or recirculation is not detrimental, and may even be desired, since the limiting reagent experiences a 100% conversion. To the contrary, in the processes carried out in the present reactors, the conversion of the limiting reagent may be less than 80% or less than 40%, or even less than 20%. Substantially increasing the conversion of such reactions is typically not desirable, since the same can result in the increased formation of by-products rather than increased formation of desired end-product. Even at such low conversions of limiting reagent, and when used to conduct reactions susceptible to the formation of by-products, the present reactors can provide selectivity to the desired product of at least about 70%, or about 75%, or about 80%, or even about 85% or greater.

One example of a design that facilitates reduced backmixing and/or recirculation zone to reduce formation of by-products during any backmixing that may occur, prior to entry into, or upon exit from, the reactor involves the use of the reactor without a mixer and/or collector, or the redesign of any mixer and/or collector desirably utilized to minimize backmixing. That is, many tubular reactors may be configured with a mixer and/or collector fluidly connected thereto, wherein reactants are provided to the reactor, or reactor effluent is dispensed therefrom, as the case may be. Backmixing may typically occur in such conventional mixers/collectors, and/or mixers/collectors arranged conventionally with respect to the reactor. One example of a conventional mixer, within which backmixing may occur, is shown in FIG. 1.

Figure 1:
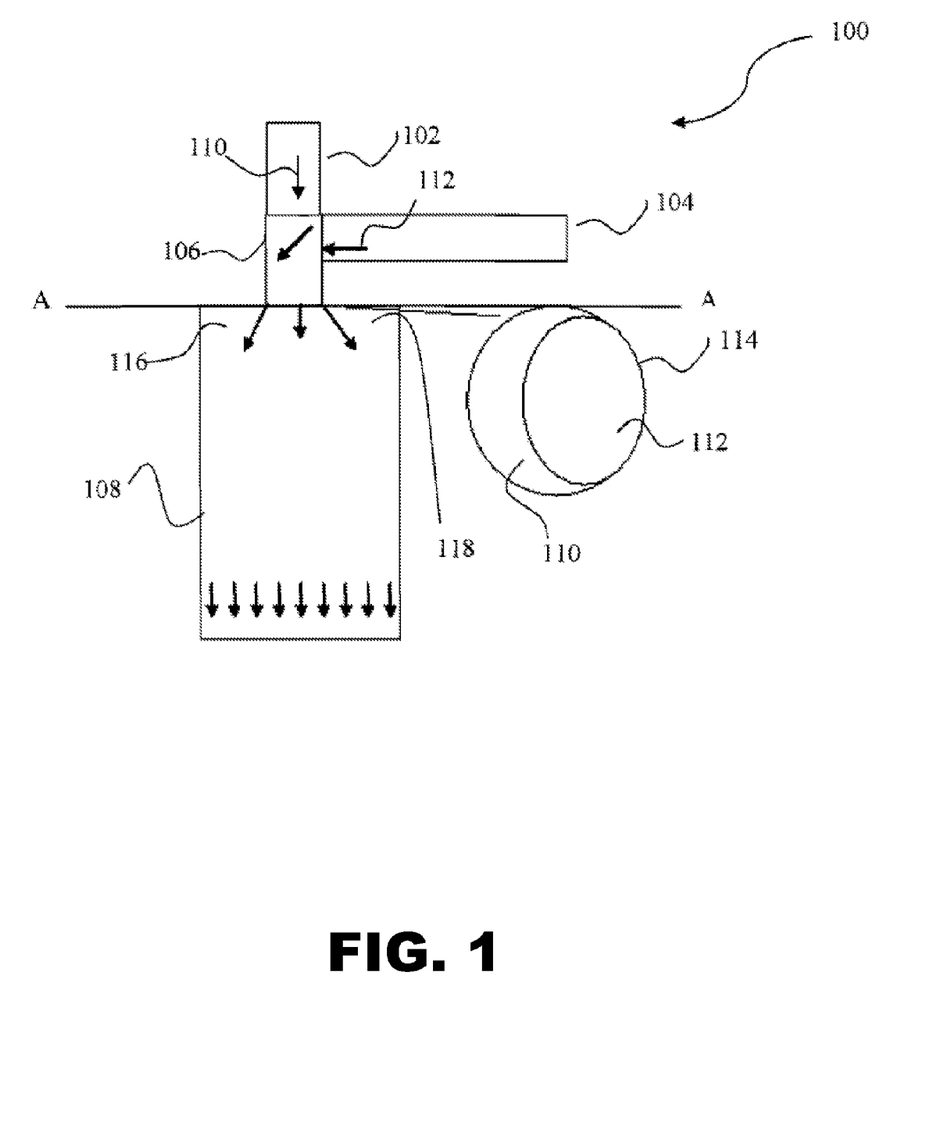
FIG. 1 is a schematic representation in cross-section of a conventional mixer.

More particularly, mixer 100 as shown in FIG. 1 is a conventional T-mixer comprising inlets 102 and 104 and conduit 106. FIG. 1 also shows reactor 108 and the relationship thereof to mixer 100. In operation, inlets 102 and 104 would be fluidly connected to feed sources (not shown) and provide feedstreams 110 and 112, respectively, of, e.g., reactants and/or diluents to and through conduit 106. Conduit 106, in turn, is fluidly connected with reactor 108.

As shown, feedstream 110 contacts feedstream 112 within conduit 106. Due to the fluid dynamics created by the perpendicular relationship of inlet 102 and inlet 104, suboptimal mixing of feedstream 110 and feedstream 112 may typically occur. Cross section 114, taken at line A-A across mixer 100, shows the relationship of feedstream 110 and feedstream 112 that may typically result from this suboptimal mixing.

Further, and because of the disparity between the diameter of mixer conduit 106 and reactor 108, the combined feedstreams 110 and 112 are expected to fan out upon entry into reactor 108 in a generally conical pattern, creating deadspaces 116 and 118, within which undesirable backmixing or recirculation may occur. In order to reduce the reactions that may occur in deadspaces 116 and 118, many conventional processes/reactions conducted in reactors comprising such a conventional mixer rely on a reduced inlet temperature at which the undesirable reactions do not occur, or occur to a lesser extent. A reduced inlet temperature, in turn, requires an increased reaction volume, which may be undesirable in many applications.

In order to reduce or eliminate any such backmixing or recirculation, the present reactors may be provided without a conventional mixer and/or collector, so that the reactants are fed substantially directly into the reactor and/or the reactor effluent is passed from the reactor directly to a liquid quench zone. Or, the diameter/shape of the reactor and any mixer and/or collector may be configured to be substantially the same, so that areas of backmixing or recirculation are not created in dead space created by disparate geometries between the reactor and collector. Any such mixer/collector will also desirably be placed about the same longitudinal axis as the reactor, so that the reactants and the reactor effluent flow in a direction substantially parallel to the longitudinal axis.

Figure 2:
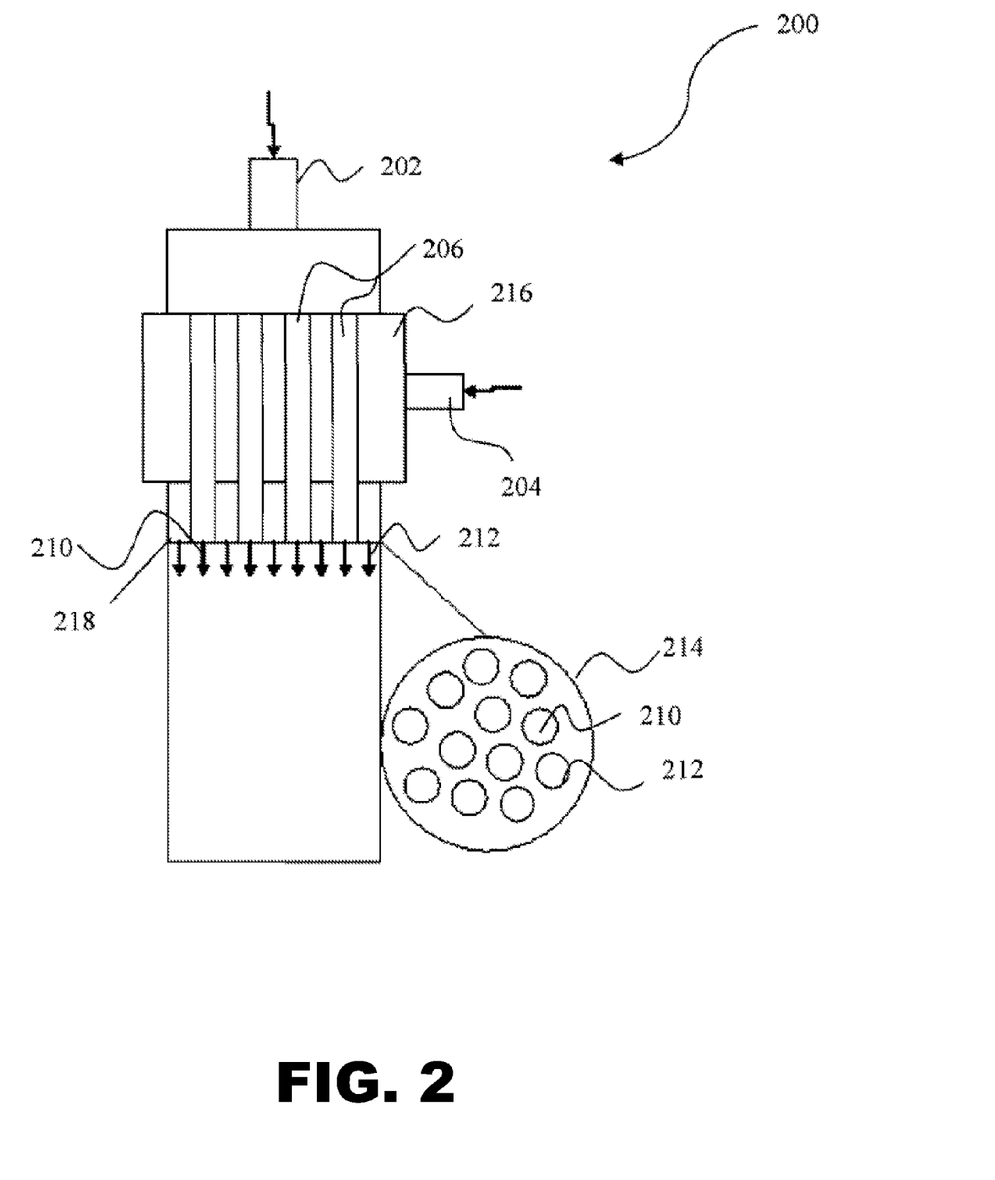
FIG. 2 is a schematic representation in cross-section of a mixer according to one embodiment of the invention.

Reduced backmixing or recirculation may also be provided by providing the reactor with a mixer design that minimizes the same. One example of such a design is shown in FIG. 2. As shown, mixer 200 is generally of a shell and tube configuration, i.e., mixer 200 comprises inlet 202 fluidly connected to tubes 206. Inlet 202 provides feedstream 210 from a feed source (not shown) to reactor 208. Mixer 200 also comprises inlet 204, which is fluidly connected to shell 216. Inlet 204 provides feedstream 212 from a feed source (not shown) therethrough to reactor 208. As a result of this configuration, feedstreams 210 and 212 are more uniformly and optimally mixed than the mixing provided by conventional mixer 100 shown in FIG. 1, as further illustrated by cross section 214 taken at interface 218. The design of mixer 200 substantially eliminates the deadspaces present in many conventional mixers (such as deadspaces 116 and 118 shown in FIG. 1), and thus, substantially eliminates backmixing that may occur in such deadspaces. As such, the temperature at the reactor inlet can be optimized for the reaction, rather than adjusted to minimize backmixing reactions.

In some embodiments, the reactor may additionally comprise one or more other design features to further minimize the formation of by-products, or to reduce or eliminate the impact of any by-products that are formed. More particularly, the reactors provided herein may comprise one or more of i) a design that minimizes heat transfer to and/or from the reactor; ii) a design that optimizes the flow of the reaction components at the boundary between the reaction components and at least a portion of at least one reactor tube wall; iii) a design that facilitates a reduction of the temperature of a reactor effluent to a temperature below which substantial formation of by-products does not occur, and/or iv) a design that allows the production rate of a reaction conducted in the reactor to be adjusted by controlling the temperature of the reactor effluent. Any number of the reactor designs described herein may be used in any combination.

The present reactors may be provided with a design that facilitates minimized heat transfer to and/or from the reactor, i.e., that facilitate the capability of the reactor to operate substantially adiabatically. The term "adiabatically" as applied to the tubular reactors described herein means that any substantial heating or cooling within the reactor is provided by the exothermic or endothermic reactions being conducted therein, with little or no heating or cooling provided from outside sources.

Various methodologies can be utilized to minimize heat transfer to and/or from the reactor. Insulating the reactor with any amount of insulation of one type, or a combination of types, in any number of layers, is but one exemplary method to minimize heat transfer. For example, utilization of an insulation having an effective thermal conductivity of 0.05 W/M/° C. is expected to maintain reagent conversion close to 10% in a reactor with 6 ft ID. Examples of insulating material with approximately this effective thermal conductivity value include, but are not limited to, wool, fiber glass wool, Kapok, rock wool, balsam wool, cardboard, corkboard, silica aerogel, wood shavings, balsa, plaster gypsum, diatomaceous earth brick, or combinations of these. In such embodiments, multiple layers of insulation may be used, with each layer having the same, or different, function(s). For example, the present reactor may comprise an insulation layer of carbon steel, brick, or ceramic to minimize corrosion and an insulation layer of a less exotic and/or costly material, such as e.g., glass wool to provide a heat transfer barrier.

Reactor diameter may also be optimized so that heat transfer to and/or from the reactor is minimized. In such embodiments, the reactor diameter may desirably be at least about 0.5 feet, or at least about 4 feet or greater, so that heat transfer to and/or from the reactor is minimized.

Increased residence time through conventional tubular reactors may also lead to the formation of undesirable by-products, and may generally occur due to the velocity gradient layer at the interface between an internal wall of a reactor tube and the reaction mixture flowing therethrough. The velocity of the reaction mixture in this layer is typically less than the velocity of the reaction mixture in the bulk velocity. Indeed, the velocity of the velocity gradient layer can approach zero at the reactor wall. Because of this lower velocity, reactants in this layer may experience longer residence time(s) during which unwanted side reactions may occur. Minimizing any such layer can assist in the optimization of the residence time of the reaction components within the reactor, and thus, reduced formation of by-products that may otherwise be formed.

And so, in certain embodiments of the reactors provided herein, the reactor(s) may be provided with a design that optimizes the flow of the reaction components within the velocity gradient layer. In one embodiment, this can be achieved by minimizing the depth/thickness of the layer, as can be achieved by providing a turbulence flow region within at least a portion of the reactor definable by a Reynolds number (Re) of at least about 2100. For generally circular configurations, the Reynolds number can be determined by the equation $$Re = \frac{4G}{\pi D \mu}$$

where G is the mass flow rate (kg/s), D is the tube inner diameter (m), and μ is the viscosity (1/kg/m/s), respectively) of at least about 2100. For example, one such embodiment may comprise providing a flow rate of about 3.6 MM#/d through a reactor having an internal diameter of about 6 ft or less is be expected to exhibit a Reynolds number of greater than 580,000 for the exemplary reaction of methyl chloride and perchloroethylene to produce 1,1,2,3-tetrachloropropene.

For embodiments of the present reactors wherein the reactor tubes are not generally circular, the Reynolds number can be determined dividing the hydraulic diameter $D_h$, which, in turn, is 4 times the cross-sectional area of flow, by the wetted perimeter, w. In such embodiments, the equation used to determine the Reynolds number would be $$Re = \frac{4G}{\pi D_h \mu},$$

wherein G is the mass flow rate (kg/s), μ is the viscosity (1/kg/m/s) and $$D_h = \frac{4A}{w}$$

where A=cross sectional area of flow and w=wetted perimeter.

The present reactors may also be provided with a design that facilitates providing a reactor effluent with a temperature that discourages reactions that form by-products in any collector provided in connection with the reactor, or as the reaction effluent is provided to a downstream process prior to a reaction zone within at least one reactor tube. Such a temperature will depend upon the reaction desirably taking place within the reactor, and it is expected that those of ordinary skill in the art will be able to determine the same. For example, in the instance of the exemplary reaction to produce 1,1,2,3-tetrachloropropene, the effluent temperature will desirably be less than 350° C., or less than 270° C., so that the methyl chloride and perchloroethylene, do not substantially react to provide by-products such as, e.g., tetrachlorobutenes, graphite and other carbonaceous deposits and/or hydrogen chloride.

The temperature of the reactor effluent is desirably reduced quickly, i.e., before any substantial amount of such by-products has had the opportunity to form. Generally speaking, and in the case of the exemplary reaction to produce 1,1,2,3-tetrachloropropene, the temperature of the reactor effluent will desirably be cooled to below 350° C. or below about 270° C. in less than about 5 seconds, or even less than about 1 second. Stated another way, the reactor effluent will desirably be cooled at a rate of at least about 20° C./sec, or 50° C./sec, or even about 100° C./sec.

The desired temperature can be affected using any suitable method of doing so at the desired rate, and in some embodiments may be accomplished via liquid quenching. In such embodiments, the quench function may be performed by any suitable method, such as, e.g., application of a temperature adjusting fluid via at least one nozzle, spray nozzle or weir nozzle.

The temperature adjusting fluid utilized in the quench function can be any suitable fluid capable of providing the desired temperature within the desired amount of time. Advantageously, the temperature adjusting fluid may be a reaction component, so that further components are not added to the process, requiring later separation and thereby adding to process cost. In some embodiments, a recycled reaction product may be utilized to perform the quench function, and may be purified, e.g., via filtration, prior to being so utilized, or may be utilized in unpurified form.

In some embodiments, the reactor provided herein may comprise a design that allows the production rate to be adjusted by controlling the temperature of the reactor effluent. Many methods of doing so are known to those of ordinary skill in the art, and any of these may be utilized in the present reactors. One exemplary method comprises providing the reactor with a design that allows for individual adjustment of the flow rate and/or temperature of one or more reactants, initiator(s), and/or diluent(s). Individual flow rate adjustment can be provided by providing separate inlets for the reaction components desirably adjusted, and further providing each inlet with an adjustable valve. And, individual temperature adjustment can be provided by providing a separate method of temperature control for each reaction component desirably controlled or adjusted. For example, individual preheaters can be provided for each reaction component for which individual temperature adjustment is desirable.

The flow rate and/or temperature provided to the reactant(s), initiator(s), and/or diluents(s) will depend upon the particular reaction being carried out, and the production rate desirably achieved. Generally speaking then, for the exemplary reaction of methyl chloride and perchloroethylene to produce e.g., 1,1,2,3-tetrachloropropene, at a production rate of from about 12 to about 47 KTA (thousands of tons per annum), flow rates of methyl chloride and perchloroethylene of from about 1.5 to about 2.0 MM#/d (millions of pounds per day) and from about 2.0 to about 2.7 MM#/d, respectively, are expected to be suitable. If an initiator, such as one comprising chlorine, is desirably used in the process, the flow rate of the same may be from about 0.20 to about 0.25 MM#/d. Appropriate temperatures to achieve such a production rate for the reactants of this particular reaction are from about 350° C. to about 500° C. for methyl chloride (preferably 400° C. to 450° C.), from about 250 to 400° (preferably) 300° C. to about 375° C. for perchloroethylene, and from about 300° C. to about 325° C. for carbon tetrachloride, if an initiator is utilized.

One or more of the improved design concepts may advantageously be employed in a reactor for use in a continuous gas phase, free-radical process and are expected to minimize production of by-products, including decomposition products, within the reactor. For example, any two of the design concepts may be employed, any three of the design concepts may be employed, any four of the design concepts may be employed, or all five of the design concepts may be employed. Whether the reactor comprises one, two, three, four or all five of the design concepts, the percent conversion of the reaction carried out within the reactor may be kept within a desired range, e.g., the percent conversion may vary by less than about 2%, or even less than about 1%, from the desired conversion, so that the desired percent selectivity may be seen.

And so, the present reactors are particularly well suited for conducting reactions for which an increase in percent conversion may typically indicate increased production of reaction by-products, and thus, reduced percent selectivity. Such reactions may also typically include at least one limiting reactant having desired conversions that are far from exhaustion, e.g., conversions of less than 80%, or less than 40%, or even less than 20%. Stated another way, at a limiting reagent conversion of at least about 5%, or at least about 10%, or at least about 15%, or even at least about 20%, selectivity to the desired product can be as high as about 70%, or about 75%, or about 80%, or even about 85% or greater. Advantageously, the reduced production of by-products can also reduce fouling of the reactor tube wall, thereby preserving reactor capacity and thus, reaction yield.

One example of a continuous, gas-phase, free radical process that may advantageously be carried out in the present reactors includes processes for the production of chlorinated and/or fluorinated alkenes comprising from about three to about six carbon atoms, in particular those making use of catalysts/initiators comprising chlorine. Such catalysts can be thermally sensitive and can degrade or otherwise undesirably react to result in reactor fouling. Further, in the exemplary reaction of methyl chloride and perchloroethylene to produce 1,1,2,3-tetrachloropropene, the reaction product itself is not only thermally unstable, but also, prone to react further with reactants and reaction by-products to form yet other by-products.

More particularly, 1,1,2,3-tetrachloropropene is reactive at 370° C. with methyl chloride and perchloroethylene, thermally unstable at 400° C.-500° C., and especially unstable at conventional reaction conditions for its production, i.e., at temperatures of from about 500° C. to about 750° C. The ensuing undesired reactions and/or decompositions lead to high concentrations of impurities, and ultimately thermal coking at these higher temperatures. For continuously fed, industrial reactors, coking is well known to cause further loss of reactor production capacity with time and often requires shutting down a reactor for cleaning and maintenance. Although the present invention is not so limited, reactions to produce 1,1,2,3-tetrachloropropene, as well as other similar reactions comprising reactants, products, diluents or byproducts with similar thermal sensitivity, are examples of those that can find particular benefit from application of the principles disclosed herein.

Processes performed in the present reactors can be provided with minimized production of by-products and/or decomposition products with at least 5% conversion of the limiting reagent or at least about 10%, or at least about 15%, or even at least about 20%, while maintaining selectivity to the desired product as high as about 70%, or about 75%, or about 80%, or even about 85% or greater. For example in the case of the production of 1,1,2,3-tetrachloropropene from methyl chloride and perchloroethylene, the limiting reagent perchloroethylene is expected to conversion to the desired product at 90% selectivity when converted at least 5%. And so, use of the present reactors in continuous processes for the production of chlorinated and/or fluorinated propene and higher alkenes can provide significant time and cost savings.

The efficiencies provided by the present reactors can be further leveraged by providing the chlorinated and/or fluorinated propene and higher alkenes produced therein to further downstream processes. For example, 1,1,2,3-tetrachloropropene produced using the described reactors can be processed to provide further downstream products including hydrofluoroolefins, such as, for example, 2,3,3,3-tetrafluoroprop-1-ene (HFO-1234yf) or 1,3,3,3-tetrafluoroprop-1-ene (HFO-1234ze). Improved methods for the production of hydrofluoroolefins, 2,3,3,3-tetrafluoroprop-1-ene (HFO-1234yf) or 1,3,3,3-tetrafluoroprop-1-ene (HFO-1234ze), are thus also provided herein.

The conversion of chlorinated and/or fluorinated propene and higher alkenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of 1,1,2,3-tetrachloropropene is fluorinated in a catalyzed, gas phase reaction to form a compound such as 2-chloro-3,3,3-tri-fluoropropene. The 2-chloro-2,3,3,3-tetrafluoropropane is then dehydrochlorinated to 2,3,3,3-tetrafluoropropene via a catalyzed, gas phase reaction.

The following examples are set forth for the purpose of illustrating the invention; but these examples are not intended to limit the invention in any manner. One skilled in the art will recognize a variety of substitutions and modifications of the examples that will fall within the scope of the invention.

Example 1 (Comparative)

A 1" ID Hastelloy reactor is heated to from about 450° C. to about 480° C. Methyl chloride and perchloroethylene flow are established at from about 50 ml/hr to about 150 ml/hr and from about 180 ml/hr to about 123 ml/hr liquid flow, respectively, to achieve a residence time of from about 10 seconds to about 23 seconds.

The liquid feeds are evaporated separately and preheated to achieve the same temperature as the reactor temperature in the feed line before they are mixed in ½" line before feeding into the reactor. The reactor pressure is set at 14.7 psia. After ½" feed line, the front section (conventional mixing zone) of the 1" reactor was filled with Rashig rings at a depth of 2 inches to provide at least approximated plug flow and proper mixing.

Within about three hours, a hot spot of about 600° C. was measured and graphite was formed in the mixing zone, plugging the reactor. It appears that the temperature and the backmixing or recirculation flow profile created in the conventional mixing area (where the ½" mixer goes into the 1" flow straightener zone filled with Rashig rings) induced unwanted reactions to produce the by-products that were deposited this zone.

This example thus shows that the existence of backmixing or recirculation in the reactor produces a very low selectivity to desired product and close to zero reactor productivity that renders the process uneconomical.

Example 2

For this example, perchloroethylene and methyl chloride are reacted in the presence of the initiator carbon tetrachloride to provide 1,1,2,3-tetrachloropropene in a reactor comprising both a design that allows the production rate to be adjusted by controlling the temperature of the reactor effluent and a design that facilitates reduced backmixing prior to entry into the adiabatic plug flow reactor. More particularly, the reactor comprises a mixer having the design shown in FIG. 2, and, separate evaporators for the perchloroethylene and methyl chloride.

Figure 3:
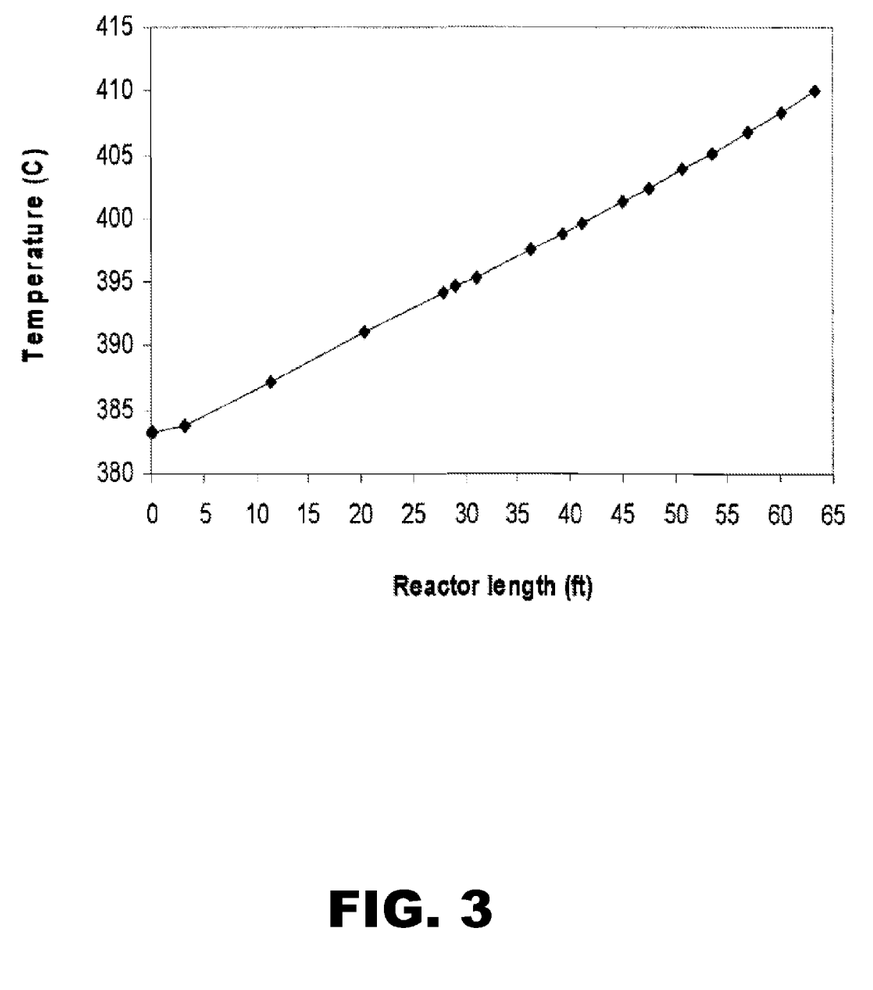
FIG. 3 is a graphical depiction of the temperature vs. reactor length in feet of an adiabatic plug flow reactor according to one embodiment of the invention.

Perchloroethylene will be introduced into a 6 foot internal diameter tubular reactor at a temperature of about 325° C. and a feed rate of about 2.65 MM#/day. Methyl chloride will be fed at a rate of 2.01 MM#/day and a temperature of 430° C., while carbon tetrachloride will be provided to the reactor at a feed rate of 0.25 MM#/day and at a temperature of 325° C. Because the perchloroethylene is set at a lower temperature than the methyl chloride stream, the reaction fluid enters the reactor at a temperature of 383° C. with the pressure of the reactor maintained at 260 psig. Because of the temperature difference between the reactants as well as the mixer design, byproduct production within the mixer is minimal. The adiabatic temperature rise is expected to be 27° C. to achieve about 10% conversion of perchloroethylene with about 90% selectivity to 1,1,2,3-tetrachloropropene to give a reactor productivity of 376 gr/l/hr. Temperature vs. reactor length data expected to be obtained from this Example is shown in FIG. 3.

Example 3

For this example, perchloroethylene and methyl chloride are reacted in the presence of the initiator carbon tetrachloride to provide 1,1,2,3-tetrachloropropene in a reactor comprising both a design that allows the production rate to be adjusted by controlling the temperature of the reactor effluent and a design that facilitates reduced backmixing and/or recirculation prior to entry into the adiabatic plug flow reactor. More particularly, the reactor utilized comprises a mixer having the design shown in FIG. 2, and, separate evaporators for the perchloroethylene/carbon tetrachloride and methyl chloride.

Methyl chloride, perchloroethylene and carbon tetrachloride were fed to a 2" ID Inconel 600 reactor at the rate of 3500-4500 SCCM, 1400-17000 SCCM, and 700-980 SCCM respectively to achieve about 30-40 seconds residence time at 260 psig.

The reactor is equipped with the mixer shown in FIG. 2. The methyl chloride stream was preheated to from about 340° C. to about 370° C. while the perchloroethylene/carbon tetrachloride stream was preheated to from about 310° C. to about 360° C. Reactor temperatures of from about 405° C. to about 415° C. resulted in a perchloroethylene conversion of from about 7.2% to about 9.6% and 1,1,2,3-tetrachloropropene selectivity of from about 87% to about 90%. The reactor productivity was found to be 80-120 gr/hr/l. After about 7 days of continuous operation, the reactor was shut down and inspected. The reaction zone was found to have a slight coating of carbon deposit.

Example 4

Chlorinated and/or fluorinated propenes having the formula $CH_{2-c-g}Cl_cF_g=CH_{1-d-h}Cl_dF_h-CH_{3-e-f}Cl_eF_f$ wherein c is 0-2, d is 0-1, e is 0-3, f is 0-3, and g is 0-2 while $c+g\leq2$, $d+h\leq1$, and $e+f\leq3$ are prepared using a reactor having a design that minimizes heat transfer to and/or from the reactor, and in accordance with Examples 2 and 3. With overall reactor volume similar to that described in Example 2, Table 1 shows that at least 10 cm insulation with effective thermal conductivity of 0.05 W/M/° C. is expected to maintain reagent conversion close to 10% in a reactor with 6 ft ID.

Table 1 also shows that removing the insulation, leaving the reactor metal wall of Inconel results in an effective thermal conductivity of 20 W/M/° C. and this is expected to drop the conversion or productivity by more than 50% if the same reactor length is used. Reducing the reactor diameter to 1 ft keeping the same reactor volume and insulation thickness the same results in about 10% drop in reactor productivity. Increasing the insulation thickness by 150% is expected to regain the productivity by 5%.

TABLE 1

| | Reactor ID (ft) | | | |
| --- | --- | --- | --- | --- |
| | 6 | 6 | 1 | 1 |
| % Perc conversion | 9.8 | 4.4 | 9.0 | 9.54 |
| Insulation thickness (cm) | 10.2 | 0 | 10.2 | 25.4 |
| effective thermal conductivity (W/M/° C.) | 0.05 | 20 | 0.05 | 0.05 |

Example 5

Chlorinated and/or fluorinated propenes having the formula $CH_{2-c-g}Cl_cF_g=CH_{1-d-h}Cl_dF_h-CH_{3-e-f}Cl_eF_f$ wherein c is 0-2, d is 0-1, e is 0-3, f is 0-3, and g is 0-2 while $c+g\leq2$, $d+h\leq1$, and $e+f\leq3$, are prepared using a reactor having a design that minimizes heat transfer to and/or from the reactor as shown in Table 2, and in accordance with Examples 2 and 3. In Table 2, and the remaining tables, "Cony" means conversion and "Sel" means selectivity.

TABLE 2

| Example | Feeds | Insulation layer 1 | Insulation layer 2 | Reactor Inner diameter (ft) | % Conv. | % Sel. |
|---|---|---|---|---|---|---|
| Comparative | $CH_{4-a-b}Cl_aF_b$ Chlorofluoroethylene | NA | NA | 6 | ≤10% | X % |
| 5A | $CH_{4-a-b}Cl_aF_b$ $CH_{4-a-b}Cl_aF_b$ | Carbon steel | NA | 0.5 | ≤15% | >X % |
| 5B | $CH_{4-a-b}Cl_aF_b$ $CH_{4-a-b}Cl_aF_b$ | Brick | NA | 1.0 | ≤15% | >X % |
| 5C | $CH_{4-a-b}Cl_aF_b$ $CH_{4-a-b}Cl_aF_b$ | Ceramic | NA | 1.5 | ≤15% | >X % |
| 5D | $CH_{4-a-b}Cl_aF_b$ $CH_{4-a-b}Cl_aF_b$ | Carbon steel | Glass wool | 2.0 | ≤15% | >X % |
| 5E | $CH_{4-a-b}Cl_aF_b$ $CH_{4-a-b}Cl_aF_b$ | Brick | Glass wool | 2.5 | ≤15% | >X % |
| 5F | $CH_{4-a-b}Cl_aF_b$ $CH_{4-a-b}Cl_aF_b$ | Ceramic | Glass wool | 3.0 | ≤15% | >X % |
| 5G | Methyl chloride perchloroethylene | Carbon steel | NA | 3.5 | ≤15% | >X % |
| 5H | Methyl chloride perchloroethylene | Brick | NA | 4.0 | ≤15% | >X % |
| 5I | Methyl chloride perchloroethylene | Ceramic | NA | 4.5 | ≤15% | >X % |
| 5J | Methyl chloride perchloroethylene | Carbon steel | Glass wool | 5.0 | ≤15% | >X % |
| 5K | Methyl chloride perchloroethylene | Brick | Glass wool | 5.5 | ≤15% | >X % |
| 5L | Methyl chloride perchloroethylene | Ceramic | Glass wool | 6.0 | ≤15% | >X % |

Example 6

Chlorinated and/or fluorinated propenes having the formula $CH_{2-c-g}Cl_cF_g=CH_{1-d-h}Cl_dF_h-CH_{3-e-f}Cl_eF_f$ wherein c is 0-2, d is 0-1, e is 0-3, f is 0-3, and g is 0-2 while c+g≤2, d+h≤1, and e+f≤3 are prepared using a reactor having a design that optimizes the flow of the reaction components within the velocity gradient layer, and in accordance with Example 2. As shown in Table 3, a large reactor inner diameter must be used to maintain a Reynolds number below 2100 and to achieve laminar flow condition even at 100× lower production rate with similar reactor volume and other operating condition as used in Example 2. This large diameter reactor and its associated mixer are likely to require higher cost to manufacture. In addition, the existence of significant variation in the velocity profile in a reactor operating at the laminar flow region is expected to result in much lower selectivity than those operating at turbulent region [R. Bird et at "Transport Phenomena," J. Wiley 1960].

TABLE 3

| Example | Feeds | Total Flow rate (1000 lb/day) | Reactor inner diameter (ft) | Reynolds # | % Sel. | % Conv. |
|---|---|---|---|---|---|---|
| 6A (Comp) | Methyl chloride Perchloroethylene | 49.1 | >16 | <2100 | <80% | >10% |
| 6B | Methyl chloride Perchloroethylene | 49.1 | 6 | 5800 | 91% | 8% |

Example 7

Chlorinated and/or fluorinated propenes having the formula $CH_{2-c-g}Cl_cF_g=CH_{1-d-h}Cl_dF_h-CH_{3-e-f}Cl_eF_f$ wherein c is 0-2, d is 0-1, e is 0-3, f is 0-3, and g is 0-2 while c+g≤2, d+h≤1, and e+f≤3, are prepared using a reactor having a design that optimizes the flow of the reaction components within the velocity gradient layer as shown in Table 4, and in accordance with Example 2.

TABLE 4

| Example | Feeds | Flow rate (M#/d) | Reactor inner diameter (ft) | Reynolds # | % Conv. | % Sel. |
|---|---|---|---|---|---|---|
| 7A | $CH_{4-a-b}Cl_aF_b$ Chlorofluoroethylene | 49.1 | >16 | <2100 | >10% | X % |
| 7B | $CH_{4-a-b}Cl_aF_b$ $CH_{4-a-b}Cl_aF_b$ | 49.1 | 6 | 5800 | 8% | >X % |

Example 8

Chlorinated and/or fluorinated propenes having the formula $CH_{2-c-g}Cl_cF_g$=$CH_{1-d-h}Cl_dF_h$—$CH_{3-e-f}Cl_eF_f$ wherein c is 0-2, d is 0-1, e is 0-3, f is 0-3, and g is 0-2 while c+g≤2, d+h≤1, and e+f≤3 are prepared using a reactor and operating conditions in accordance with Example 3.

Example 8A (Comparative)

The reactor effluent is at a temperature of from about 410° C. to about 420° C. and is cooled to a temperature of from about 270° C. to about 350° C. at a residence time of about less than 10 seconds before being condensed in a 0.5 inch ID cooling coil at temperature of less than about 80° C. After a week of run time at low perchloroethylene conversion of from about 3.8% to about 5.0%, the reactor is severely fouled in the cool down zone and the condensing coil and is shutdown due to plugging.

Example 8B

Replacing the cool down zone and condensing coil with a liquid spray quench chamber resulted in run time of more than two weeks at twice the limiting reagent conversion. Opening the reactor shows no fouling in the spray quench chamber. This shows that rapid quenching of greater than 15° C./s minimizes fouling in the product quenching zone.

Example 9

Chlorinated and/or fluorinated propenes having the formula $CH_{2-c-g}Cl_cF_g$=$CH_{1-d-h}Cl_dF_h$—$CH_{3-e-f}Cl_eF_f$ wherein c is 0-2, d is 0-1, e is 0-3, f is 0-3, and g is 0-2 while c+g≤2, d+h≤1, and e+f≤3 are prepared using a reactor having a design that facilitates providing a reactor effluent with a temperature that discourages reactions that form by-products as shown in Table 5, and also in accordance with Example 3.

TABLE 5

| Example | Feeds | Effluent cooling rate (° C./sec) | Effluent cooled temperature (° C.) | Cooling method | % Conversion | % Selectivity |
|---|---|---|---|---|---|---|
| Comp. | $CH_{4-a-b}Cl_aF_b$ Chlorofluoroethylene | NA | NA | NA | X % | X % |
| 9A | $CH_{4-a-b}Cl_aF_b$ $CH_{4-a-b}Cl_aF_b$ | 20 | 375 | nozzle | X % + ≤5% | >X % |
| 9B | $CH_{4-a-b}Cl_aF_b$ $CH_{4-a-b}Cl_aF_b$ | 50 | 350 | Spray nozzle | X % + ≤5% | >X % |
| 9C | $CH_{4-a-b}Cl_aF_b$ $CH_{4-a-b}Cl_aF_b$ | 100 | 325 | Weir nozzle | X % + ≤5% | >X % |
| 9D | Methyl chloride perchloroethylene | 20 | 375 | nozzle | X % + ≤5% | >X % |
| 9E | Methyl chloride perchloroethylene | 50 | 350 | Spray nozzle | X % + ≤5% | >X % |
| 9F | Methyl chloride perchloroethylene | 100 | 325 | Weir nozzle | X % + ≤5% | >X % |

Example 10

Figure 4:
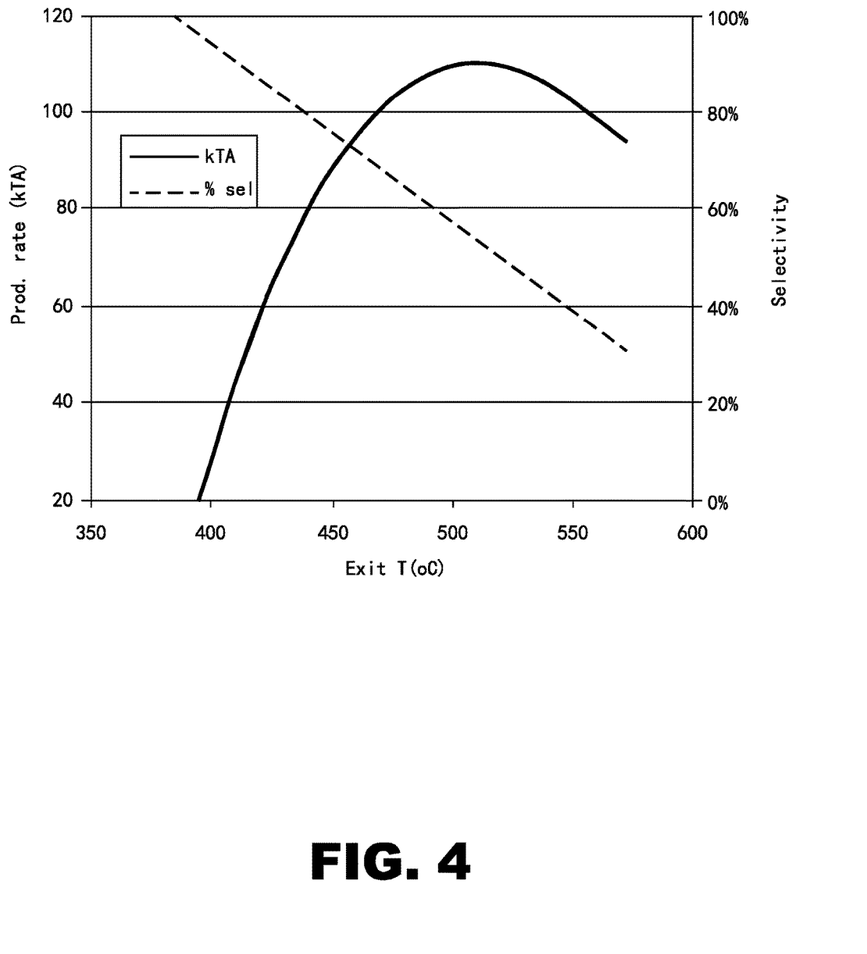
FIG. 4 is a graphical depiction of the production rate and selectivity, versus the exit reactor temperature.

Chlorinated and/or fluorinated propenes having the formula $CH_{2-c-g}Cl_cF_g$=$CH_{1-d-h}Cl_dF_h$—$CH_{3-e-f}Cl_eF_f$ wherein c is 0-2, d is 0-1, e is 0-3, f is 0-3, and g is 0-2 while c+g≤2, d+h≤1, and e+f≤3 are prepared using a reactor having a given volume and a design that allows the production rate to be adjusted by controlling the temperature of the reactor effluent, and also in accordance with Example 2. Table 6, below, shows that while the production rate can be expected to be independently adjusted by adjusting the exit reactor temperature, the selectivity to the product tends to decline at higher temperature. In fact, at temperature higher than 500° C., the selectivity will be expected to be so low that the production rate starts to decline. Thus, it is desirable to operate at lower than 450° C. to maintain selectivity higher than about 70% to provide low raw material cost. Table 6 also shows that at the exit reactor temperature less than 450° C., the methyl chloride (R1) and perchloroethylene (R2) flow rates and their corresponding temperatures can also be adjusted to obtain the desired production rate while maintaining high selectivity to the desired product. This is also shown by FIG. 4.

TABLE 6

| Example | R1 temp (° C.) | R1 flow rate (MM#/d) | R2 temp (° C.) | R2 flow rate (MM#/d) | Selectivity | Exit T (° C.) | Production rate (kTA) |
|---|---|---|---|---|---|---|---|
| 10A | 430 | 2.01 | 325 | 2.65 | 89% | 411 | 46 |
| 10B | 400 | 2.01 | 360 | 3.65 | 92% | 396 | 35 |
| 10C | 410 | 4.01 | 360 | 2.65 | 92% | 412 | 44 |

Example 11

Chlorinated and/or fluorinated propenes having the formula $CH_{2-c-g}Cl_cF_g=CH_{1-d-h}Cl_dF_h—CH_{3-e-f}Cl_eF_f$ wherein c is 0-2, d is 0-1, e is 0-3, f is 0-3, and g is 0-2 while c+g≤2, d+h≤1, and e+f≤3, are prepared using a reactor having a given volume and a design that allows the production rate to be adjusted by controlling the temperature of the reactor effluent, and also in accordance with Example 2. For Examples 7A through 7C, reactant 1 (R1) $CH_{4-a-b}Cl_aF_b$ and reactant 2 (R2) is a chlorofluoroethylene.

TABLE 7

| Example | R1 temp (° C.) | R1 flow rate (MM#/d) | R2 temp (° C.) | R2 flow rate (MM#/d) | Selectivity | Exit Temp (° C.) | % Conversion |
|---|---|---|---|---|---|---|---|
| 11A | 430 | 2.01 | 325 | 2.65 | 89% | 411 | 46 |
| 11B | 400 | 2.01 | 360 | 3.65 | 92% | 396 | 35 |
| 11C | 410 | 4.01 | 360 | 2.65 | 92% | 412 | 44 |

Example 12

Hydrofluoroolefins are prepared from the chlorinated and/or fluorinated propenes prepared according to Examples 1-4 by any of several methods known in the art. For example, the conversion of 1,1,2,3-tetrachlororopropene to HFO-1234yf using HF with Chromium/Cobalt base catalyst may be prepared in accordance with the methodology described in WO2008054781A1. WO 2009003084 describes a multi-step process wherein a feedstock of 1,1,2,3 tetrachloropropene is fluorinated in a liquid phase without a catalyst followed by a catalyzed, gas phase reaction to form 2-3,3, 3-tetrafluoropropene (HFO1234yf) that is also suitable. US20090030244A1 describes the production of HFO-1234yf using 1,1,2,3-tetrachloropropene using a catalytic process with HF with HCFC-1233xf as intermediate, and this process may also be used. Finally, US20090099396A1 describes a suitable a liquid phase catalytic reaction followed by gas-phase reaction of 1,1,2,3-tetrachloropropene with HV with HFC-245eb as an intermediate. Each of these patent documents is hereby incorporated by reference herein in its entirety for any and all purposes.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A process for producing a chlorinated and/or fluorinated propene, having the formula $CH_{2-c-g}Cl_cF_g=CH_{1-d-h}Cl_dF_h—CH_{3-e-f}Cl_eF_f$ wherein c is 0-2, d is 0-1, e is 0-3, f is 0-3, g is 0-2 and h is 0-1, while c+g≤2, d+h≤1, and e+f≤3 which process comprises providing a feed comprising methanes, chloromethanes, fluoromethanes, or chlorofluoromethanes, having the formula $CH_{4-a-b}Cl_aF_b$, wherein each a and b are independently 0-3 and 4-a-b is greater than 0, and a chloroethylene or chlorofluoroethylene in an adiabatic plug flow reactor wherein the reactor is operably disposed relative to a mixer having a diameter and shape that are the same as those of the reactor, the reactants flow through the mixer, and the reactor further comprises a collector having the same shape and/or diameter as the reactor; wherein a turbulence flow region exists within at least a portion of the reactor having a Reynolds number (Re) of at least 2100, wherein the adiabatic plug flow reactor further comprises at least one of i) an insulation material, ii) a temperature controller for the reactor effluent; or iii) one or more temperature and flow controllers for one or more reactants, initiator(s) and/or diluents; wherein the reactor provides reduced backmixing and/or recirculation prior to entry into, or upon exit from, the reactor.

2. The process of claim 1, wherein the reactor comprises a collector configured to accept a reactor effluent from the reactor and further configured to minimize backmixing and/or recirculation.

3. The process of claim 1, wherein the reactor comprises a mixer configured to accept one or more reactants, initiators, and/or diluents and further configured to minimize backmixing and/or recirculation of the same.

4. The process of claim 1, wherein the reactor inlet temperature is at least 370° C. or the reactor productivity is at least 40 gr/hr/l.

5. The process of claim 1, wherein the reactor
   i. minimizes heat transfer to and/or from the reactor;
   ii. optimizes the flow of the reaction mixture at a boundary between the reaction mixture and at least a portion of at least one reactor tube wall;
   iii. facilitates a reduction of the temperature of a reactor effluent to a temperature below which substantial formation of by-products does not occur, and/or
   iv. allows the production rate in the reactor to be adjusted by controlling the temperature of the reactor effluent.

6. The process of claim 5, wherein the reactor
   i. minimizes heat transfer to and/or from the reactor;
   ii. optimizes the flow of the reaction mixture at a boundary between the reaction mixture and at least a portion of at least one reactor tube wall;
   iii. facilitates a reduction of the temperature of a reactor effluent to a temperature below which substantial formation of by-products does not occur, and iv. allows the production rate in the reactor to be adjusted by controlling the temperature of the reactor effluent.

7. The process for preparing 2,3,3,3-tetrafluoroprop-1-ene (HFO-1234yf) or 1,3,3,3-tetrafluoroprop-1-ene (HFO-1234ze) comprising preparing 1,1,2,3-tetrachloropropene by the process of claim 1, and converting the 1,1,2,3-tetrachloropropene into 2,3,3,3-tetrafluoroprop-1-ene (HFO-1234yf) or 1,3,3,3-tetrafluoroprop-1-ene (HFO-1234ze).

8. The process for preparing 2,3,3,3-tetrafluoroprop-1-ene (HFO-1234yf) or 1,3,3,3-tetrafluoroprop-1-ene (HFO-1234ze) comprising preparing 1,1,2,3-tetrachloropropene by the process of claim 2, and converting the 1,1,2,3-tetrachloropropene into 2,3,3,3-tetrafluoroprop-1-ene (HFO-1234yf) or 1,3,3,3-tetrafluoroprop-1-ene (HFO-1234ze).

9. The process for preparing 2,3,3,3-tetrafluoroprop-1-ene (HFO-1234yf) or 1,3,3,3-tetrafluoroprop-1-ene (HFO-1234ze) comprising preparing 1,1,2,3-tetrachloropropene by the process of claim 3, and converting the 1,1,2,3-tetrachloropropene into 2,3,3,3-tetrafluoroprop-1-ene (HFO-1234yf) or 1,3,3,3-tetrafluoroprop-1-ene (HFO-1234ze).

10. The process for preparing 2,3,3,3-tetrafluoroprop-1-ene (HFO-1234yf) or 1,3,3,3-tetrafluoroprop-1-ene (HFO-1234ze) comprising preparing 1,1,2,3-tetrachloropropene by the process of claim 4, and converting the 1,1,2,3-tetrachloropropene into 2,3,3,3-tetrafluoroprop-1-ene (HFO-1234yf) or 1,3,3,3-tetrafluoroprop-1-ene (HFO-1234ze).

11. The process for preparing 2,3,3,3-tetrafluoroprop-1-ene (HFO-1234yf) or 1,3,3,3-tetrafluoroprop-1-ene (HFO-1234ze) comprising preparing 1,1,2,3-tetrachloropropene by the process of claim 5, and converting the 1,1,2,3-tetrachloropropene into 2,3,3,3-tetrafluoroprop-1-ene (HFO-1234yf) or 1,3,3,3-tetrafluoroprop-1-ene (HFO-1234ze).

12. The process for preparing 2,3,3,3-tetrafluoroprop-1-ene (HFO-1234yf) or 1,3,3,3-tetrafluoroprop-1-ene (HFO-1234ze) comprising preparing 1,1,2,3-tetrachloropropene by the process of claim 6, and converting the 1,1,2,3-tetrachloropropene into 2,3,3,3-tetrafluoroprop-1-ene (HFO-1234yf) or 1,3,3,3-tetrafluoroprop-1-ene (HFO-1234ze).

13. The process of claim 2, wherein the reactor comprises a mixer configured to accept one or more reactants, initiators, and/or diluents and further configured to minimize backmixing and/or recirculation of the same.

14. The process of claim 13, wherein the chlorinated and/or fluorinated alkane and chlorinated and/or fluorinated alkene is selected from methanes, chloromethanes, fluoromethanes, or chlorofluoromethanes, having the formula $CH_{4-a-b}Cl_aF_b$, wherein each a and b are independently 0-3 and 4-a-b is greater than 0.

* * * * *